United States Patent
Jatana et al.

(10) Patent No.: US 12,245,910 B2
(45) Date of Patent: Mar. 11, 2025

(54) PROTECTIVE MOUTH ASSEMBLY AND METHOD OF OPERATION

(71) Applicant: Research Institute at Nationwide Children's Hospital, Columbus, OH (US)

(72) Inventors: Kris R. Jatana, Columbus, OH (US); Charles A. Elmaraghy, Columbus, OH (US)

(73) Assignee: The Research Institute at Nationwide Children's Hospital, Columbus, OH (US)

(*) Notice: Subject to any disclaimer, the term of this patent is extended or adjusted under 35 U.S.C. 154(b) by 41 days.

(21) Appl. No.: 17/687,233

(22) Filed: Mar. 4, 2022

(65) Prior Publication Data

US 2022/0265390 A1    Aug. 25, 2022

Related U.S. Application Data

(63) Continuation of application No. 15/575,671, filed as application No. PCT/US2016/033723 on May 23, 2016, now Pat. No. 11,284,968.

(60) Provisional application No. 62/165,293, filed on May 22, 2015, provisional application No. 62/215,874, filed on Sep. 9, 2015.

(51) Int. Cl.
*A61C 5/90*    (2017.01)
*A61B 90/00*    (2016.01)

(52) U.S. Cl.
CPC .......... *A61C 5/90* (2017.02); *A61B 2090/036* (2016.02)

(58) Field of Classification Search
CPC ......... Y10S 602/902; A61C 7/08; A61C 5/90; A63B 71/085; A61F 5/566; A61F 5/56; A61B 2090/036; A61B 1/32; A61B 1/24; A61M 16/0497; A61M 16/0493
See application file for complete search history.

(56) References Cited

U.S. PATENT DOCUMENTS

| | | | |
|---|---|---|---|
| 3,241,550 | A | 3/1966 | Gelarie |
| 4,024,859 | A | 5/1977 | Slepyan et al. |
| 4,200,089 | A | 4/1980 | Inoue |
| 4,543,950 | A | 10/1985 | Keys, Jr. |
| 6,241,521 | B1 | 6/2001 | Garrison |

(Continued)

FOREIGN PATENT DOCUMENTS

WO    WO 02/07636    1/2002

OTHER PUBLICATIONS

International Search Report and Written Opinion of the International Search Authority Dated Aug. 23, 2016 (10 pgs).

*Primary Examiner* — Ophelia A Hawthorne
(74) *Attorney, Agent, or Firm* — Watts Law LLC; John A. Yirga, Esq.

(57) ABSTRACT

An adjustable protective mouth assembly and method for protecting the surroundings adjacent to the oral cavity of a patient is provided. The adjustable protective mouth assembly includes a channeled body having first and second legs spaced and integrally coupled by a connecting portion. The channeled body is for inserting into the oral cavity of a patient during use. The channeled body further having first and second ends, such that the channeled body of the first end is constructed to be received and nest within the channeled body of the second end, forming a connection therebetween.

21 Claims, 23 Drawing Sheets

(56) References Cited

U.S. PATENT DOCUMENTS

| | | | | |
|---|---|---|---|---|
| 7,866,314 B2* | 1/2011 | Isenberg | ............ | A61B 1/00165 |
| | | | | 128/207.14 |
| 11,284,968 B2 | 3/2022 | Jatana et al. | | |
| 2014/0275803 A1 | 9/2014 | Cushner et al. | | |
| 2014/0332009 A1* | 11/2014 | Haider | .............. | A61M 16/0497 |
| | | | | 128/207.14 |

* cited by examiner

PROTECTIVE MOUTH ASSEMBLY AND METHOD OF OPERATION

CROSS REFERENCES TO RELATED APPLICATIONS

The following application is a continuation application claiming priority under 35 U.S.C. § 120 to U.S. Nonprovisional patent application Ser. No. 15/575,671 filed Nov. 20, 2017 and published as U.S. Publication No.: 2018/0280117 that published on Oct. 4, 2018, which also claims priority to and is a National Stage Application claiming priority under 35 U.S.C. § 371 to International Patent Application Ser. No. PCT/US16/33723 filed May 23, 2016 that published as International Publication No.: WO 2016/191345 on Dec. 12, 2016, which further claims priority under 35 U.S.C. § 119 (e) to co-pending U.S. Provisional Patent Application Ser. No. 62/165,293 filed May 22, 2015 entitled PROTECTIVE MOUTH ASSEMBLY AND METHOD and U.S. Provisional Patent Application Ser. No. 62/215,874 filed Sep. 9, 2015 entitled PROTECTIVE MOUTH ASSEMBLY AND METHOD. The above-identified applications and publications from which priority is claimed are both incorporated herein by reference in their entireties for all purposes.

TECHNICAL FIELD

The present disclosure generally relates to the healthcare field, and more particularly to a protective mouth assembly formed as a disposable device acting as a substantially annular surround for covering a patient's lips and skin to reduce or prevent tissue injury during surgical procedures.

BACKGROUND

During oral surgery a need exists to introduce surgical instruments into the oropharyx, larynx, hypopharynx, nasopharynx, or oral cavity. During insertion, a patient's mouth is typically held open using a mouth gag or retractor. An example of an oral retractor, how it is used, and how it is constructed is further described and shown in U.S. Pat. No. 4,024,859 entitled MOUTH GAG HAVING THREE DIMENSIONAL ALVEOLUS RETRACTOR ADJUSTABILITY and 3,241,550 entitled MOUTH RETRACTOR. The aforementioned patents are incorporated herein by reference in there entireties.

Surgical instruments such as sharp or heated instruments, for example scalpels and electrocautery, respectively are generally used in performing oral or throat surgery, such as a tonsillectomy and/or adenoidectomy. In some oral surgeries, drills are used, which can contain a revolving shaft. Other types of surgical instruments are also known that may also pose a potential injury risk. Once the patient's mouth is secured open using a retractor, the patient's lips, adjacent tissue, and/or skin becomes exposed to such instruments, and at times unfortunately results in oral commisure/lip lacerations and/or burns during the most common procedures. At times, resulting tissue injuries including, but not limited to oral commisure/lip lacerations and/or burns, bruising, and scars can lead to permanent cosmetic deformities during surgical procedures involving the mouth or throat.

SUMMARY

One aspect of the present disclosure comprises an adjustable protective mouth assembly and method for protecting a portion of the oral cavity and surround of a patient is provided having a channeled body comprising first and second legs spaced and integrally coupled by a connecting portion. The channeled body is for inserting into an opening of the oral cavity of a patient during use. The channeled body further comprises first and second ends, such that the channeled body of the first end is constructed to be received and nest within the channeled body of the second end, forming a connection therebetween.

Another aspect of the present disclosure includes a method of constructing an adjustable protective mouth assembly for protecting the surroundings adjacent to the oral cavity of a patient. The method comprising the step of forming a connecting portion, forming a first leg comprising a first end, the first end constructed to be received by and nest within a second end of a second leg to form a connection, and forming the second leg comprising the second end, the second end constructed to receive and nest the first end. The method further comprises integrally coupling the connecting portion to the first leg and the second leg, such that the connecting portion spaces the first leg and the second leg, to form a channeled body for inserting into the oral cavity of a patient during use.

Another aspect of the present disclosure includes an adjustable protective mouth assembly for protecting the oral cavity and surround of a patient. The adjustable protective mouth assembly comprises a channeled body having a first leg and a second leg spaced and integrally coupled by a joint of a connecting portion. The channeled body is for inserting into the oral cavity of a patient during use. The channeled body further includes a first end and a second end, such that the channeled body of the first end is constructed to be received and nest within the channeled body of the second end to form a connection therebetween the first end and the second end. The first end further includes a first tapered portion and the second end comprises a second tapered portion, such that when the connection is formed, the first tapered portion and the second tapered portion are oriented to conform to an inner portion of a patient's upper lip to further form a continuous adjustable protective mouth assembly.

BRIEF DESCRIPTION OF THE DRAWINGS

The foregoing and other features and advantages of the present disclosure will become apparent to one skilled in the art to which the present disclosure relates upon consideration of the following description of the disclosure with reference to the accompanying drawings, wherein like reference numerals, unless otherwise described refer to like parts throughout the drawings and in which.

Figure 1:
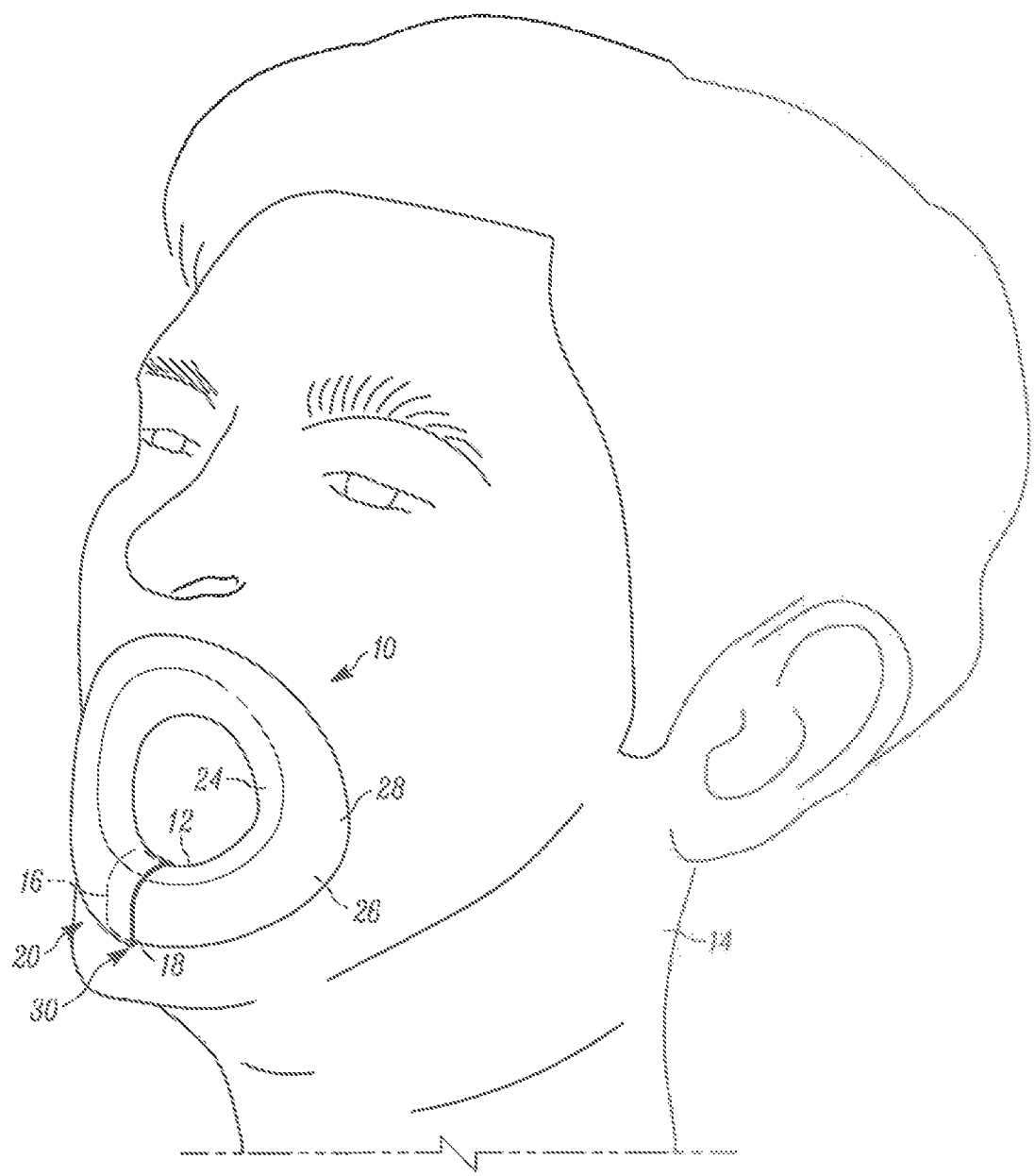
FIG. 1 is a first perspective view of a protective mouth assembly inserted for use in a patient in accordance with one example embodiment of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Referring now to the figures generally wherein like numbered features shown therein refer to like elements throughout unless otherwise noted. The present disclosure generally relates to the healthcare field, and more particularly to a protective mouth assembly formed as a disposable device acting as a substantially annular surround for covering a patient's lips and skin to reduce or prevent injury during surgical procedures.

FIGS. 1-4 illustrate a protective mouth assembly 10 constructed in accordance with one example embodiment of the present disclosure. The protective mouth assembly 10 in the illustrated example embodiment is designed to protect a patient's lips and further can be customized such that the single assembly will fit any size mouth opening of the oral cavity of any size patient. Moreover, the assembly 10 can be used with or without mouth retractors and the assembly is placed at the beginning of any surgical procedure in this region of the body. Such procedures include, but are not limited to, tonsillectomies, adenoidectomy, dental procedures, cleft lip or cleft palate procedures, and the like.

In accordance with another example embodiment, the assembly 10 is constructed in such that it is disposable after a single use. That is, the construction takes into consideration reducing fabrication costs associated with manufacturing each assembly 10. Thus, the opportunity to spread bacteria, germs or diseases is eliminated, since each assembly is disposable and used only once by one patient before being discarded. Moreover, such construction eliminates the need for sterilization.

In an alternative example embodiment, the assembly 10 is constructed from a material conducive to sterilization. That is, the assembly 10 will withstand heat, pressure, washing and other operations used in sterilizing medical devices.

FIG. 1 illustrates the assembly positioned in the oral cavity 12 of a patient 14 in accordance with one example embodiment. The assembly 10 protects the patient's entire lip surface, commissure, and skin from abrasions, mechanical trauma, lacerations when various instruments are inserted during surgical procedures. In addition, the assembly 10 is constructed from a substantially thermal resistant material in order to act as a thermal barrier (such as electrocautery burns in the range of 400° F./205° C.) between the surgical instruments and the skin. The assembly 10 is used with or without a mouth retractor. The example embodiment of FIG. 1 is used and inserted into the opening of the oral cavity 12 with or without the use of a retractor.

Figure 2A:
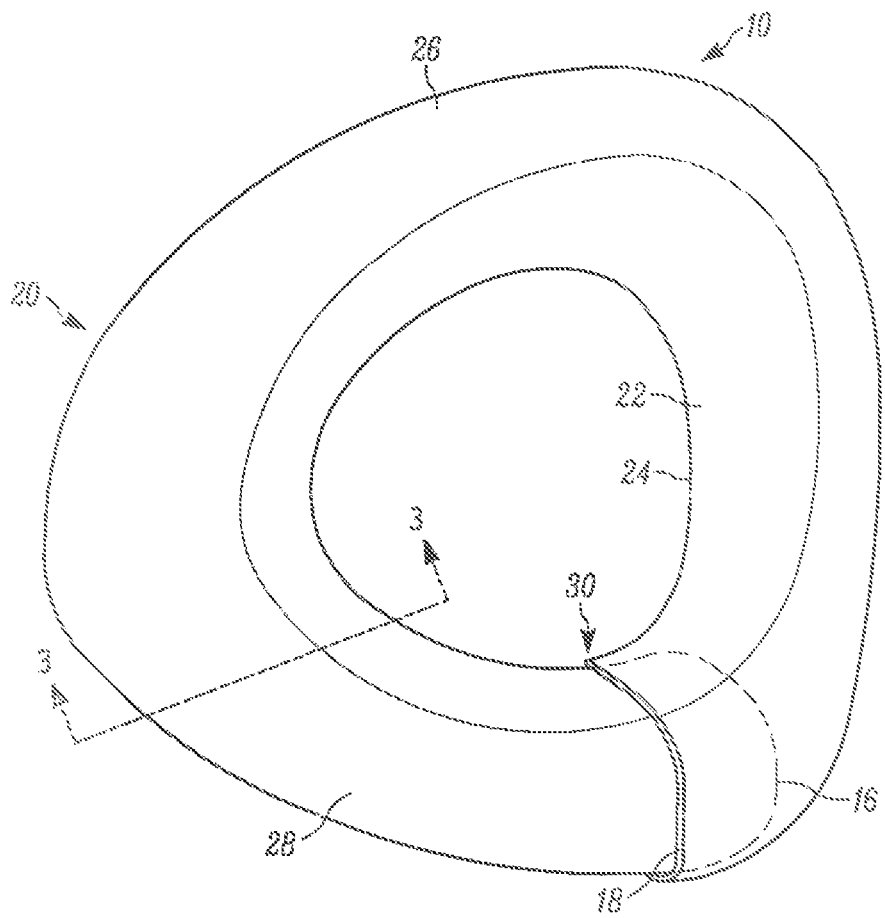
FIG. 2A is a second perspective view of the protective mouth assembly illustrated in FIG. 1.
Figure 2B:
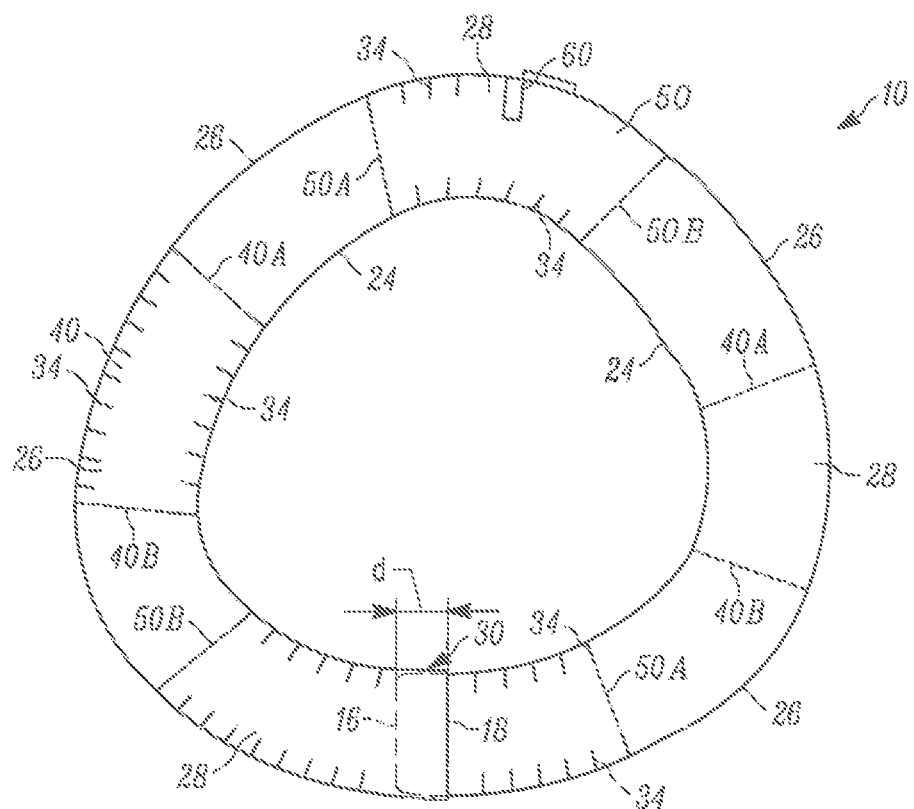
FIG. 2B illustrates a front elevation view of FIG. 1.
Figure 2C:
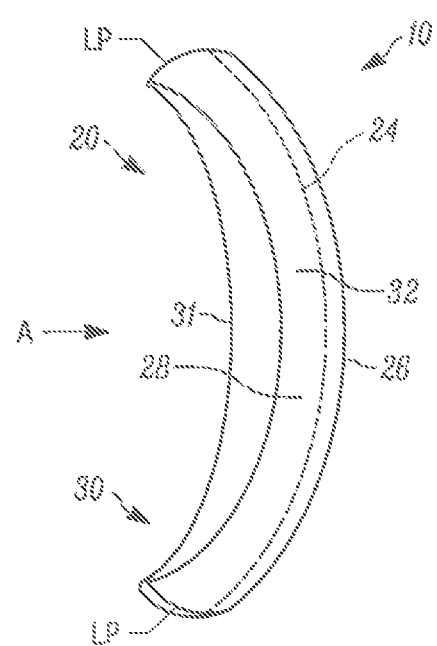
FIG. 2C illustrates a side elevation view of FIG. 1.

FIGS. 2A, 2B, and 2C further illustrate the assembly in various views in accordance with the first example embodiment. The assembly in FIGS. 1 and 2 is a single part molded thermal plastic radially biased to a substantially oval shape 20 for opening a mouth as illustrated in FIG. 1. The substantially oval shape 20 (see FIGS. 2A-2C) is formed by overlapping a first end 16 with a second end 18 of a channeled body 22 to form a connection 30 of the now continuous oval-shaped loop 20. It should be appreciated that a bellowed joint could be added to the assembly 10 opposite the connection 30 as shown in further embodiments. The channeled body 22 is formed from first and second legs 24 and 26, respectively while spaced and integrally connected when molded with a connecting portion 28. The adjustable assembly's channeled body 22 is formed from a polymeric material and when assembled as shown in FIG. 2A is substantially oval shaped with a concave bias (see FIG. 2C) along first and second sides S1 and S2 relative to a upper UP and lower portion LP as indicated by arrow A.

Figure 3:
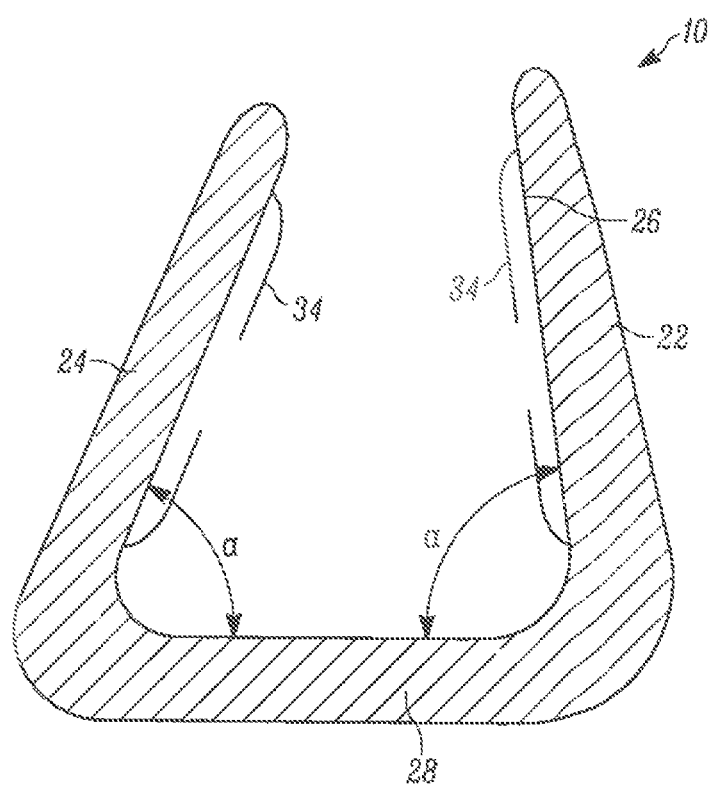
FIG. 3 is a section view along FIG. 2A identified by section lines 3-3.

In one example embodiment, the legs 24 and 26 in situ are formed with an acute angle with the connecting portion 28, as indicated by angle alpha (α) in FIG. 3, yet the legs remain flexible enough to bend over the patients' lips when inserted in the patient's oral cavity. In an alternative example embodiment, the acute angle alpha (α) can be decreased on the first leg 24 in order to provide more holding power in the oral cavity by placing more pressure on the inner lip surface. As well, the acute angle alpha (α) can be increased to an obtuse angle on the second leg 26 in order to provide more surface coverage protection to the lips or skin of the patient. In the illustrated example embodiment of FIG. 1, the connecting portion 28 and second leg 26 collectively cover slightly over 1 cm of the patients lip/skin.

Figure 4:
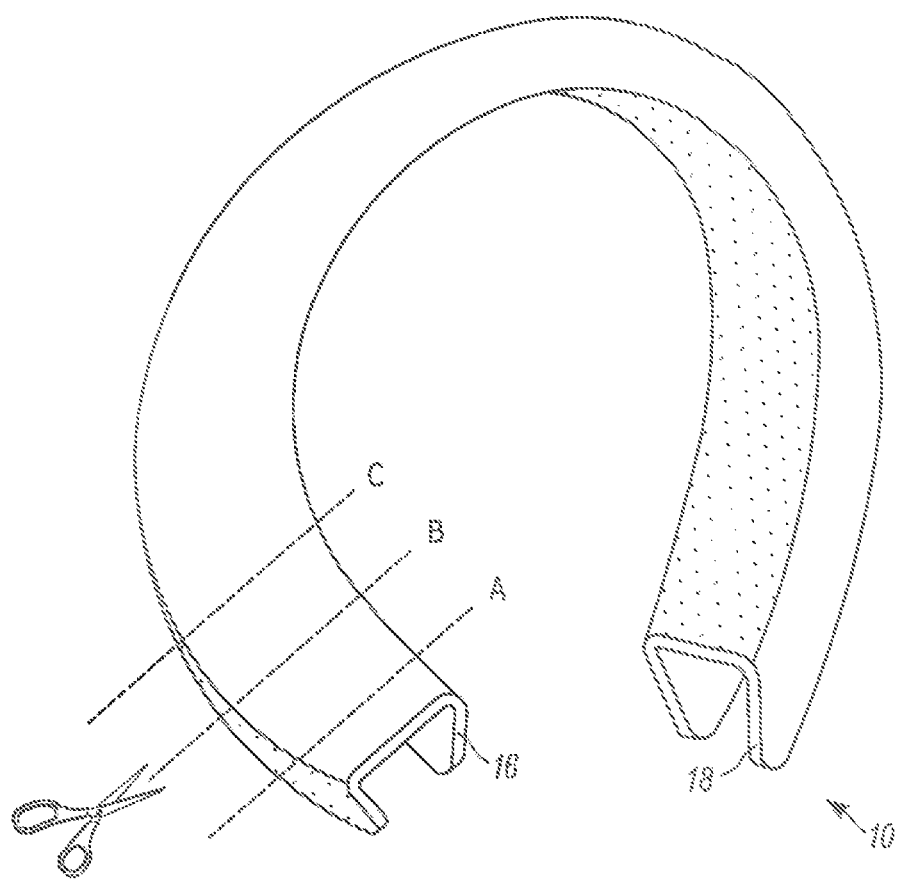
FIG. 4 is an assembly view of the protective mouth assembly being sized for a patient.
Figure 5:
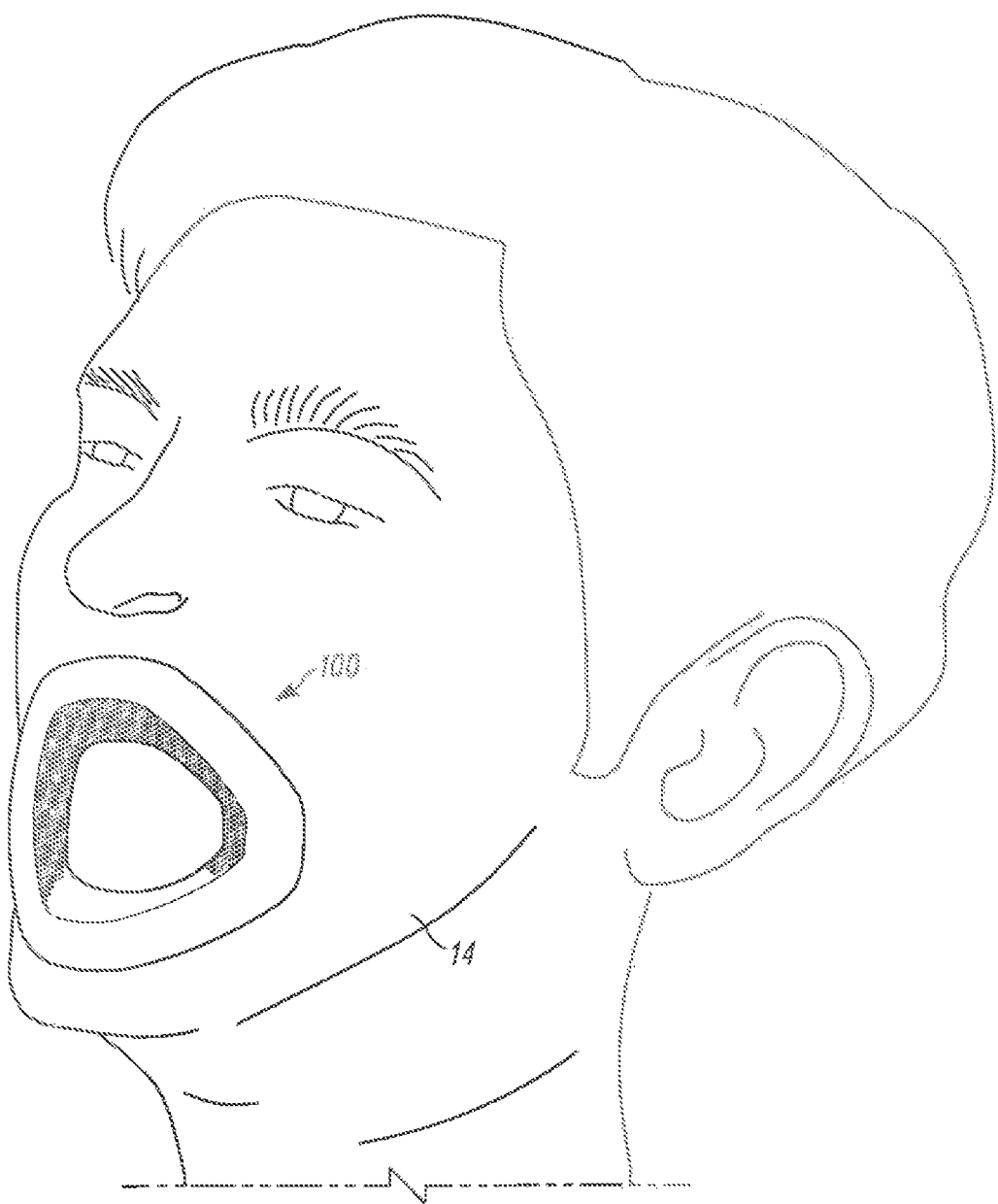
FIG. 5 is a first perspective view of a protective mouth assembly inserted for use in a patient in accordance with another example embodiment of the present disclosure.
Figure 6:
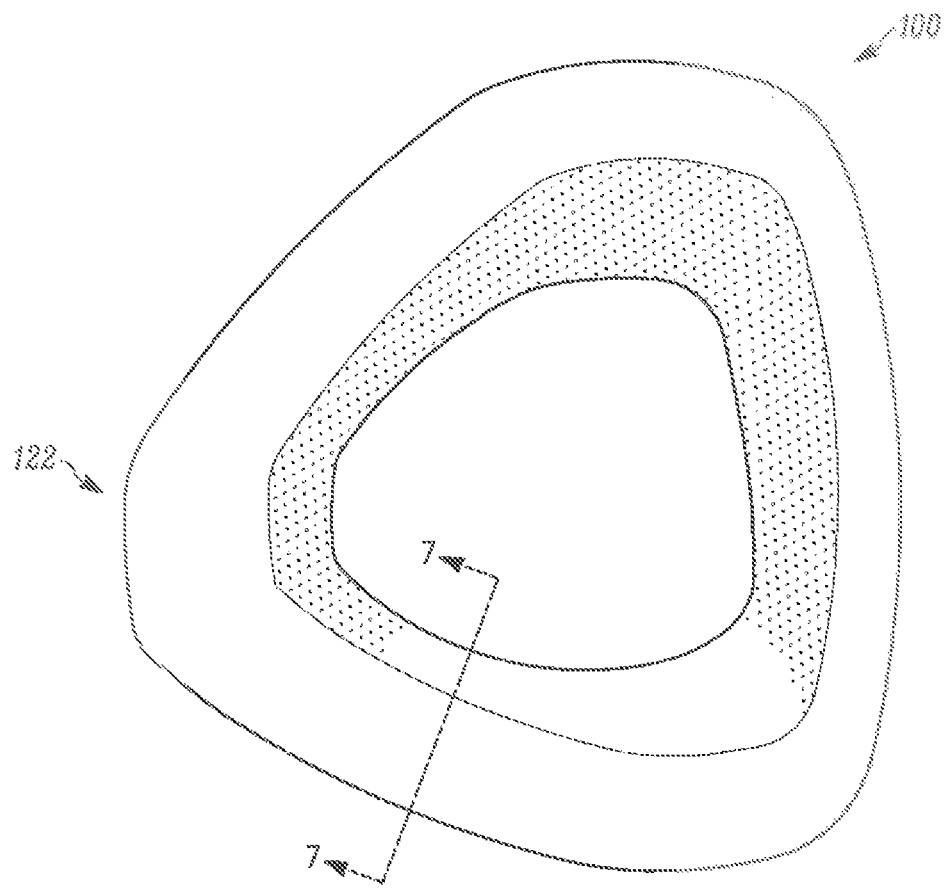
FIG. 6 is a second perspective view of the protective mouth assembly illustrated in FIG. 5.
Figure 7:
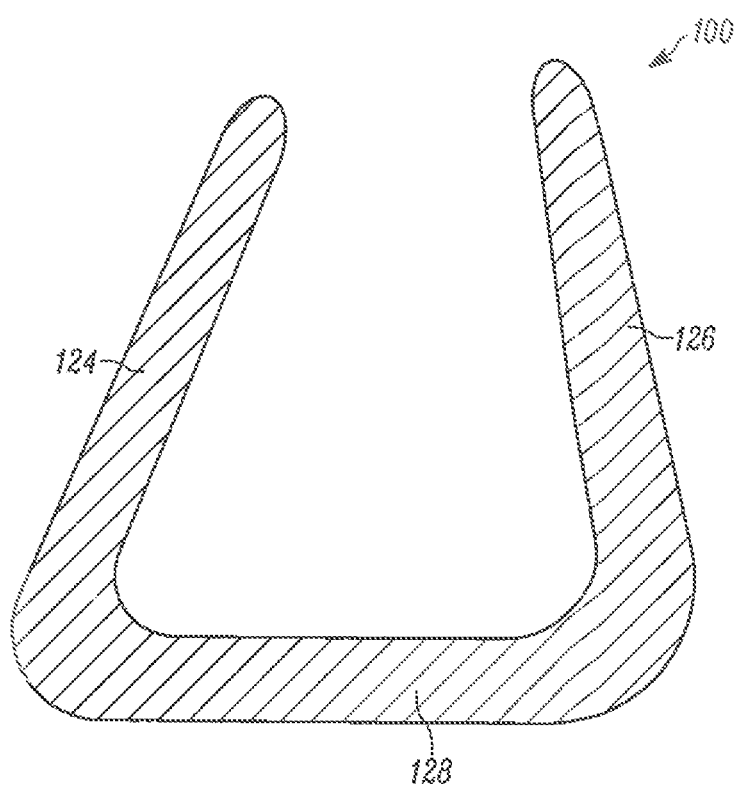
FIG. 7 is a section view of FIG. 6 along section lines 7-7.
Figure 10:
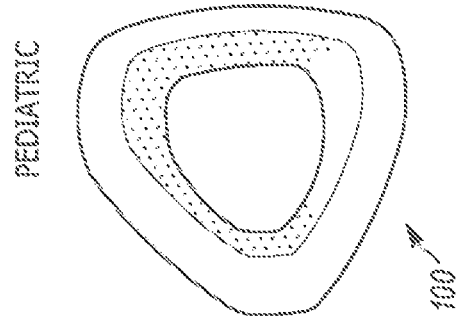
FIGS. 8-10 are perspective views of different sized protective mouth assemblies, for adult, youth, and pediatric patients.
Figure 9:
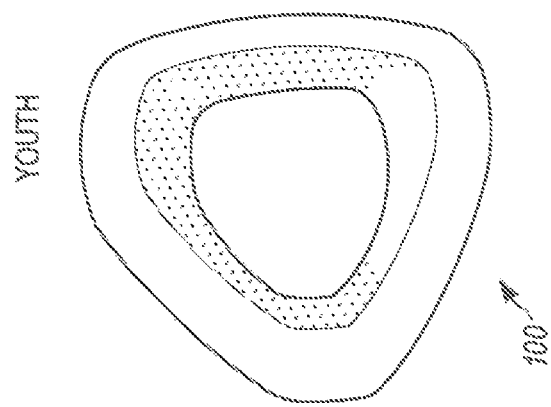
Figure 8:
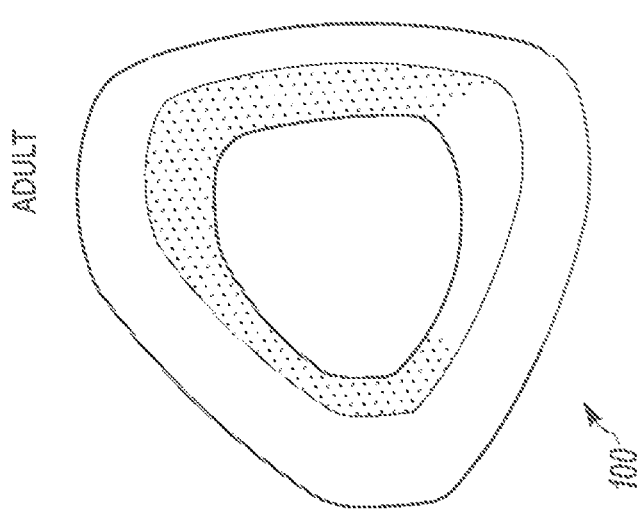

Turning now to FIG. 4, the protective mouth assembly is sized for a patient before surgery. The channeled body 22 when pulled from a mold and has a discontinuous oval-like shape and bias as illustrated in FIG. 4. The patient's size and age is considered by the surgeon or other medical personnel and the assembly 10 is cut such that a sufficient amount of overlap is provided (such as 1-5 cm) to form the connection 30 as indicated by dimension "d" in FIG. 2B. Alternatively, the connection 30 could be greater than 1-5 cm because of the telescopic geometrical construction that allows one end to nest within the other end, the sizing can be easily adjusted both to overlap more or less.

In one example embodiment, the mold provides cut lines along and molded into the body 22 such as cut lines A, B, and C shown in FIG. 4. The surgeon or medical personnel may cut the body 22 with a knife or scissors to the proper lines after sizing the patient or considering the patient's age. For example, the medical personnel will use cut line A for a pediatric patient, cut line B for a youth patient, and cut line C for an adult. Alternatively, the surgeon may position the discontinuous oval around the perimeter of the patient's mouth to determine the amount of channel required to be cut away in order to leave a sufficient overlap of 1-5 cm at the connection 30.

In the illustrated example embodiment, the assembly 10 is constructed of a nonconductive polymeric material. One suitable example of such polymeric material includes silicone having a durometer of 40 on a Shore A scale and a thickness of 2-3 millimeters (mm). In an alternative example embodiment, the legs 24 and 26 further comprise a plurality of ribs or serrations 34 along the top and bottom regions 50 divided by boundary lines 50A and 50B and side regions 40 divided by boundary lines 40A and 40B. The ribs 34 in the top and bottom regions 50 and the side regions 40 allow the channel 22 to more easily stretch over the lips of the patient and not fold on the patient's lips.

While the connection 30 is shown in the bottom region 50, it could be placed at any other location along the oval-shaped body channeled body 22. In another example embodiment, the protective assembly is transparent and/or translucent so that the patient's mouth can be seen when instruments or a retractor is inserted into the patient. While in another example embodiment, the, thickness of the connecting portion 28 is two or three times thicker than the legs 24 and 26, thus providing flexibility to the thinner legs, while increasing the protective area covered by the connecting portion 28. The channel body 22 is molded as would be appreciated by those skilled in the art to be substantially oval when connected at connection 30 (see FIGS. 2 and 4) to form the general profile to an open mouth and shape and durometer to further help bias the patient's mouth open (see FIG. 1).

In an alternative example embodiment, the channel body 22 includes an indicator 60 to assist the surgeon in orienting the assembly when inserting it into the patient's oral cavity. For example, the indicator 60 could be used to be positioned directly in line with the patient's nose. While in another example embodiment, the channel body 22 at the first end 16 includes a smaller overall width to fit within the wider channel of the second end 18. Yet in another example embodiment, the first and second ends 16, 18 include ribs along the inner and outer surfaces of the legs 24, 26 and/or the connecting portion 28 such that the ends lock when the connection 30 is formed by placing one channel within the other as illustrated in FIGS. 2A-2C.

Referring now to FIGS. 5-10 is another example of a protective mouth assembly 100 constructed in accordance with another example embodiment of the present disclosure. As can be appreciated by FIGS. 5-10, the assembly 100 is a continuously fixed oval shape 122, thus requiring various fixed sizes based on the size of the patient. For example, an adult would use the larger assembly size shown in FIG. 8, while a youth child would likely use the assemblies in FIGS. 9 and 10, respectively.

Figure 11:
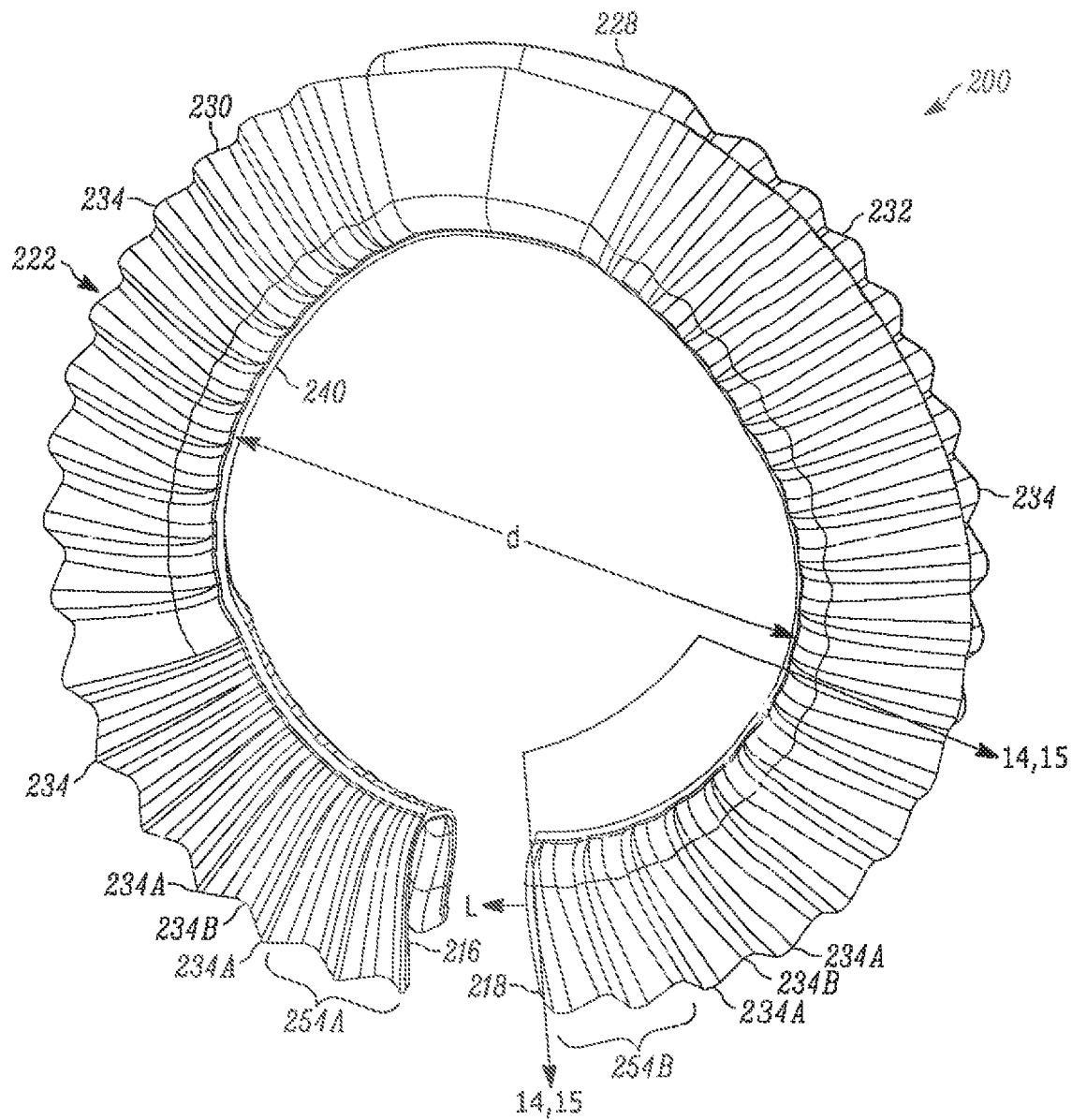
FIG. 11 is a perspective view of a protective mouth assembly constructed in accordance with an example embodiment of the present disclosure.
Figure 12:
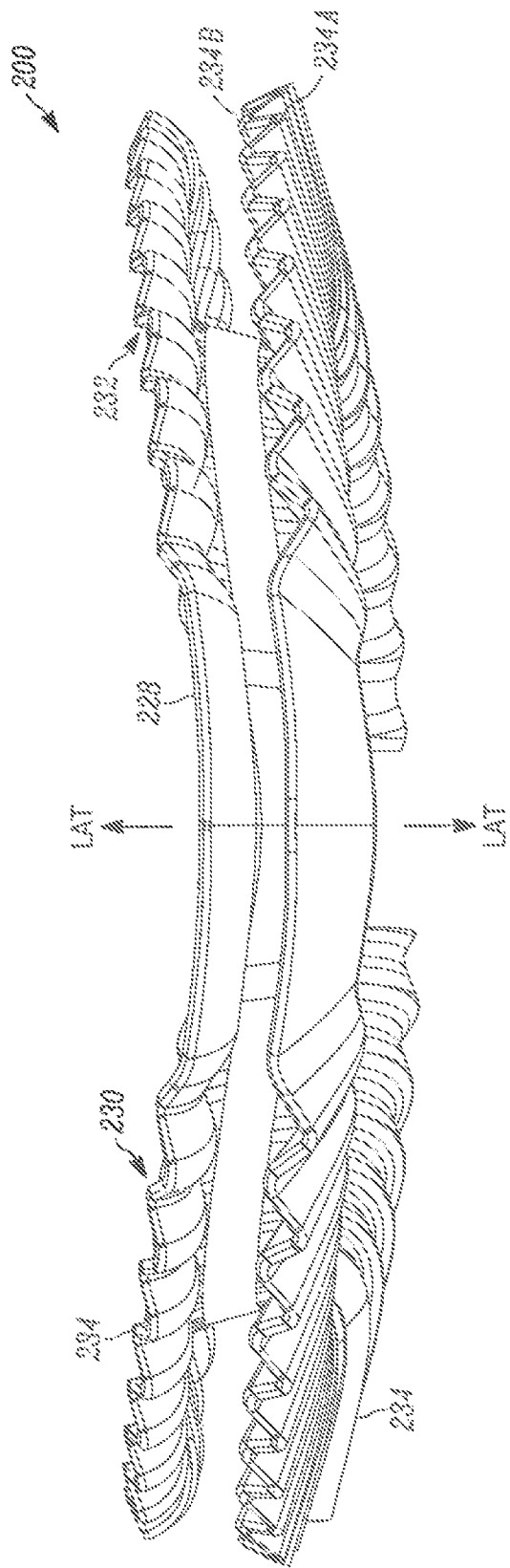
FIG. 12 is a top perspective view of FIG. 11.

FIG. 11 is a perspective view of a protective mouth assembly 200 constructed in accordance with another example embodiment of the present disclosure. The protective mouth assembly 200 in the illustrated example embodiment is designed to protect a patient's lips and further can be customized such that the single assembly will fit any size mouth opening of the oral cavity of any size patient, as illustrated in FIG. 1. Moreover, the assembly 200 can be used with or without mouth retractors. The assembly 200 is placed at the beginning of any surgical procedure in the oral region of the body. Such procedures include, but are not limited to, tonsillectomies, adenoidectomy, dental procedures, cleft lip or cleft palate procedures, and the like.

Figure 19:
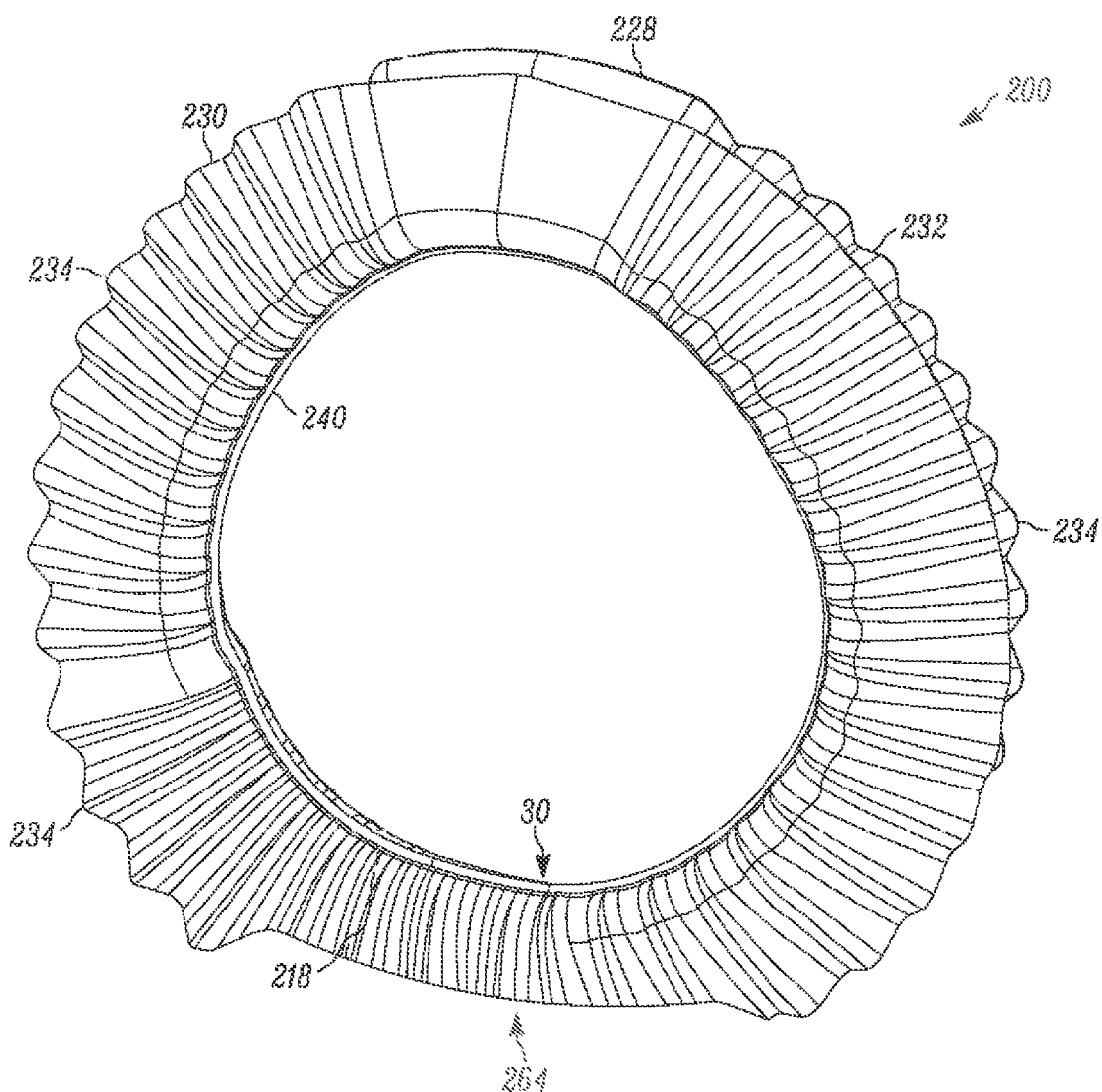
FIG. 19 is a perspective view of a protective mouth assembly constructed in accordance with an example embodiment of the present disclosure, wherein, a first end of the protective mouth assembly is nested within a second end of the protective mouth assembly.

The substantially oval shape of the assembly 200 when inserted into a patient's mouth is formed by overlapping a first end 216 with a second end 218 of a channeled body 222 to form a connection 30, as illustrated in FIGS. 1 and 19. In one example embodiment, the assembly 200 is annular and discontinuous to form a discontinuous annular assembly 200. The channeled body 222 is formed from polymeric material, such as silicone having a durometer of 40 on a Shore A scale and a thickness of 2-3 millimeters (mm).

Figure 13:
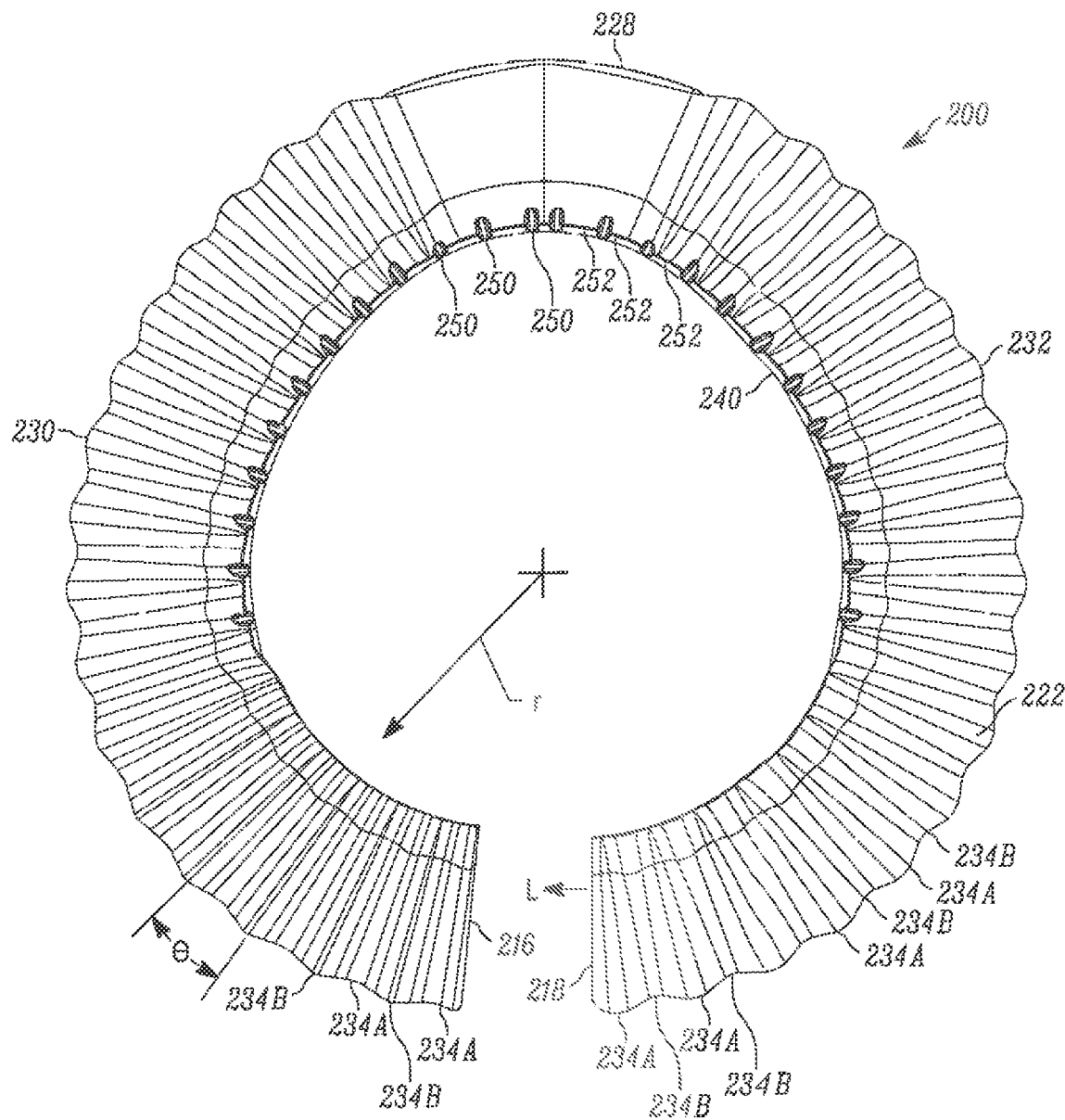
FIG. 13 is a front elevation view of FIG. 12.
Figure 14:
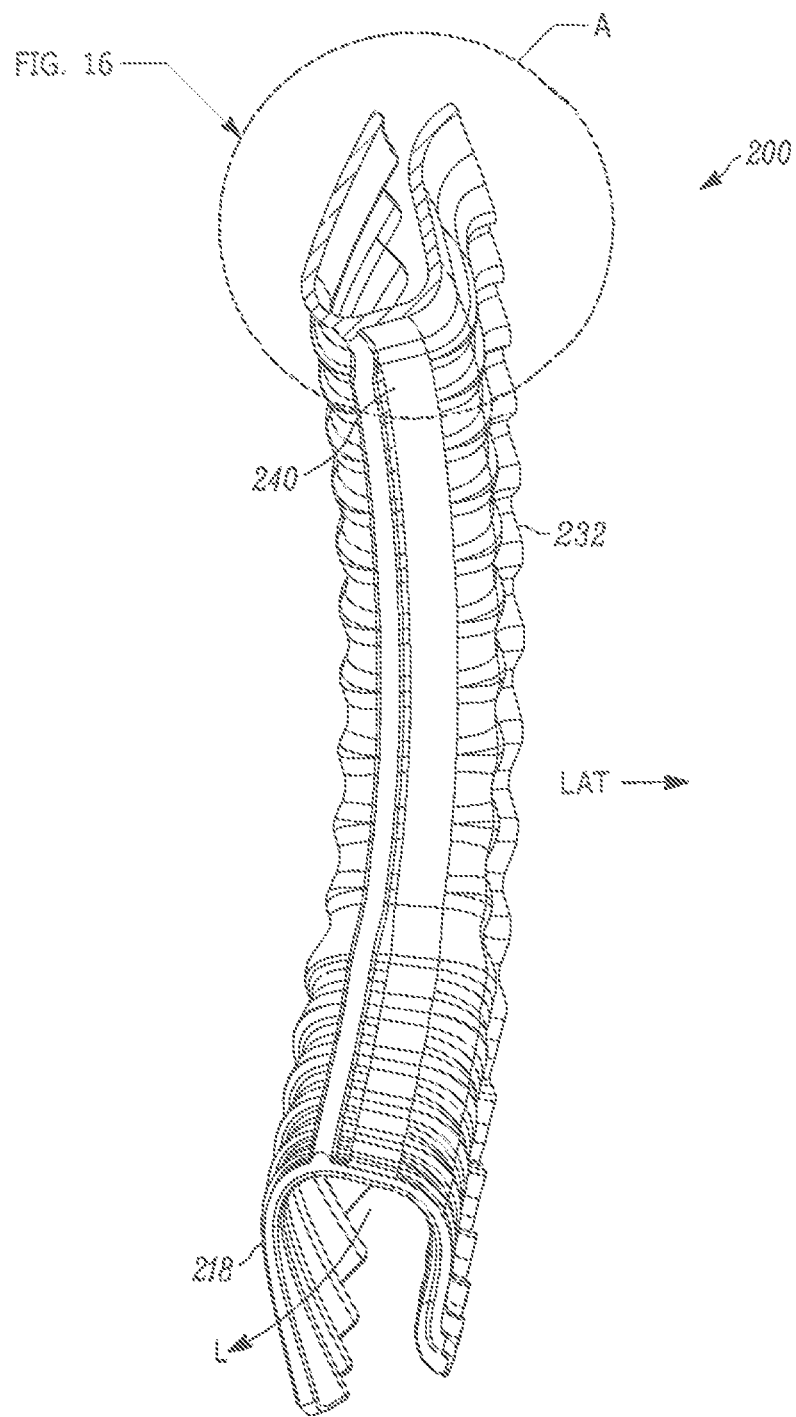
FIG. 14 is an inner section view of FIG. 11 along line 14-14.

The discontinuous annular assembly 200 includes a first leg 230 and a second leg 232, integrally coupled by a connecting portion 228, having a plurality of ribs or undulations 234 that expand radially outward "r" at an angle θ, as illustrated in FIG. 13. The ribs 234 provide overlapping locking support when the first end 216 is sized and positioned within the second end 218 once in the patient's mouth, as illustrated in FIG. 1. In one example embodiment, the first end 216 comprises a series of ribs 254A formed to nest within a matching series of ribs 254B comprised on the second end 218. That is, crests 234A and valleys 234B of the ribs 234 of the first leg 230 interlocks with the corresponding crests 234A and valleys 234B of the second leg 232 (see FIGS. 11 and 13), to prevent slipping or separation once the assembly 200 is positioned within the patient's mouth. In addition, the ribs 234 outwardly widening and bellows like action prevents buckling of the assembly 200 along an inner radial surface 240 when the assembly 200 is reduced in size to fit within a smaller or pediatric patient's mouth.

As best seen in FIG. 13, a plurality of ridges or risers 250 are formed into the radial inner surface 240. The risers 250 laterally extend along a lateral axis "LAT" of the assembly 200 transverse to a longitudinal axis "L" of the assembly. The risers 250 provide a greater material thickness to the assembly 200 to prevent instruments from compromising the assembly 200 by burning or cutting, while un-elevated spaces 252 between the risers 250 provide for maximum flexibility of the assembly 200 to accommodate differences in patient's mouth sizes.

Figure 15:
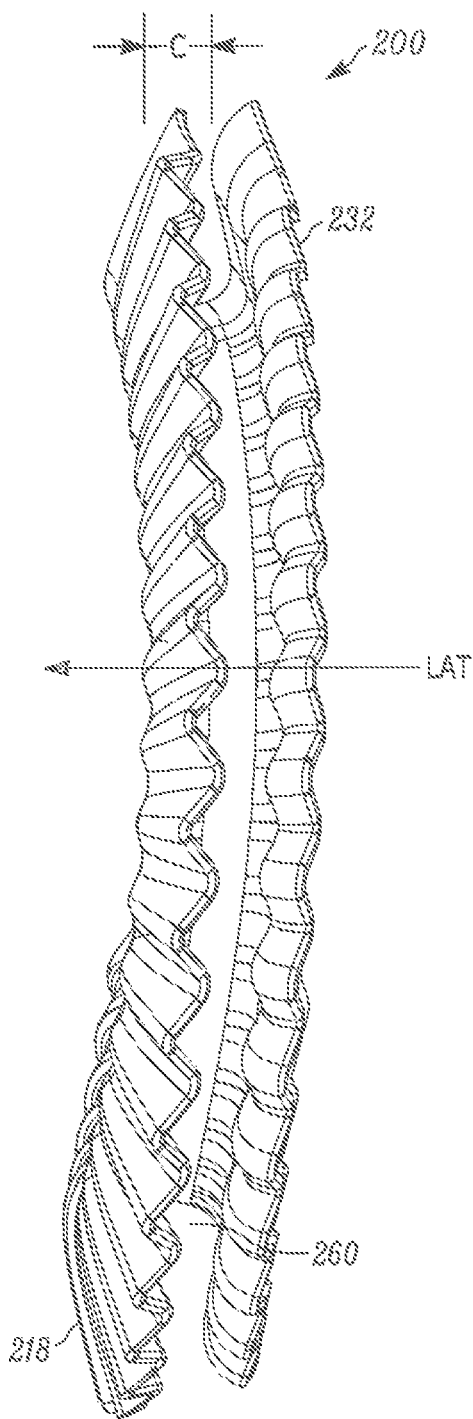
FIG. 15 is a outer section view of FIG. 11 along line 15-15.
Figure 16:
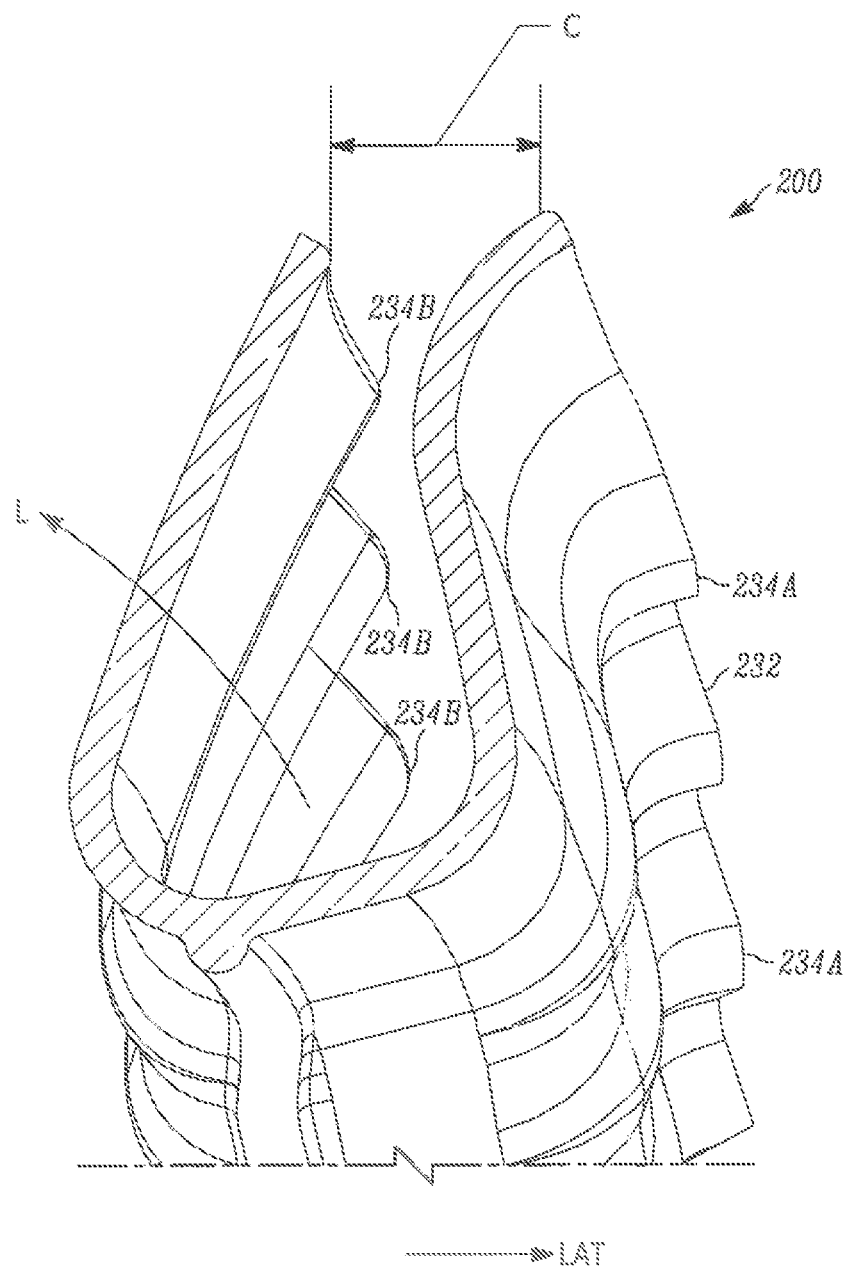
FIG. 16 is a magnified view of detail A of FIG. 14.

In one example embodiment, such as illustrated in FIG. 13, the risers or ridges 250 are two to four (2-4) mm in length laterally across the inner radial surface 240 and approximately an additional one (1) mm higher or one (1) mm thicker along the inner radial surface 240. In another example embodiment, as illustrated in FIGS. 11 and 15, the assembly 200 has an inner radial diameter "d" of between approximately six and three tenths (6.3) centimeters (cm) to six and four tenths (6.4) cm and is approximately between nine and six tenths (9.6) cm to nine and seven tenths (9.7) cm across a channel 260 "C" formed for receiving the patient's lips.

Figure 17:
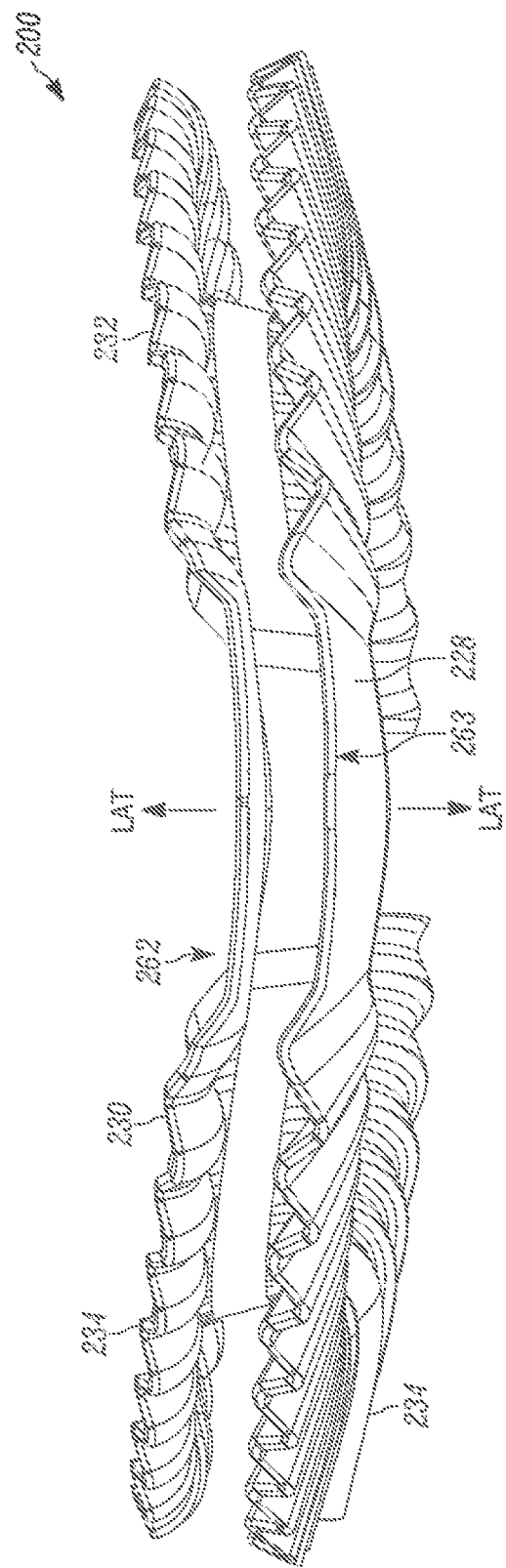
FIG. 17 is a top perspective view of a protective mouth assembly comprising a tapered portion in accordance with an example embodiment of the present disclosure.

In one example embodiment, the adjustable protective mouth assembly 200 is inserted into the patient's mouth such that the connecting portion 228 is beneath a nose of the patient and the connection 30 is formed along a bottom lip of the patient, as illustrated in FIG. 1. It should be appreciated that the connection 30 and connecting portion 228 could be oriented at any location throughout the mouth without departing from the spirit of the present disclosure. In one example embodiment, such as illustrated in FIG. 17, the connecting portion 228 comprises a tapered portion 262. The tapered portion 262 comprises an area having a shorter protrusion from the inner radial surface 240, relative to the rest of the channeled body 222. The tapered portion 262 may be oriented to conform to an inner portion of the patient's upper lip. For example, when the mouth retractor is retracted within the patient's mouth, the patient's upper lip may be shortened such that the tapered portion 262 allows for an improved fit relative to the shortened upper lip. In one example embodiment, an outer tapered portion 263 is formed in the connecting portion 228, the outer tapered portion 263 may be laterally opposite of the tapered portion 262. In an example embodiment, a midline of the upper lip is substantially centrally located about the tapered portion 262 and/or the outer tapered portion 263. The shortening of the upper lip may shorten a distance between the upper lip and the nose. The outer tapered portion 263 may improve a fit of the adjustable protective mouth assembly 200 relative to the nose of the patient (e.g., by creating space for the nose). It is understood that the connecting portion 228 may comprise the tapered portion 262, the outer tapered portion 263, or both. It should be appreciated that the tapered portion 262 and/or the outer tapered portion 263 could be located at other positions within the mouth without departing from the spirit of the present disclosure. Moreover, in another example embodiment, the assembly 200 could have multiple tapered portions 262, 263 around the perimeter of the assembly.

Figure 18:
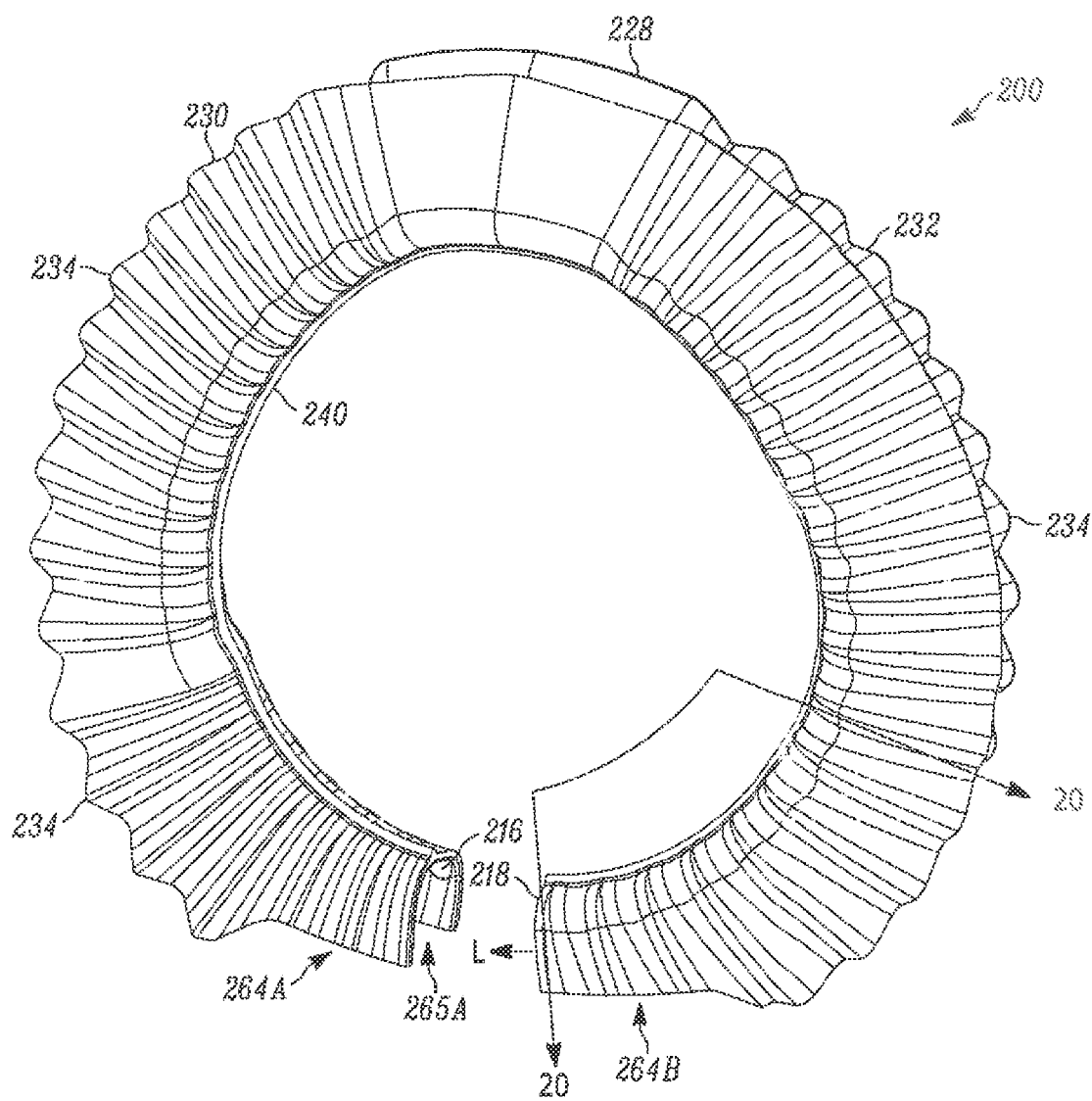
FIG. 18 is a perspective view of a protective mouth assembly comprising a first tapered portion and a second tapered portion constructed in accordance with an example embodiment of the present disclosure.
Figure 20:
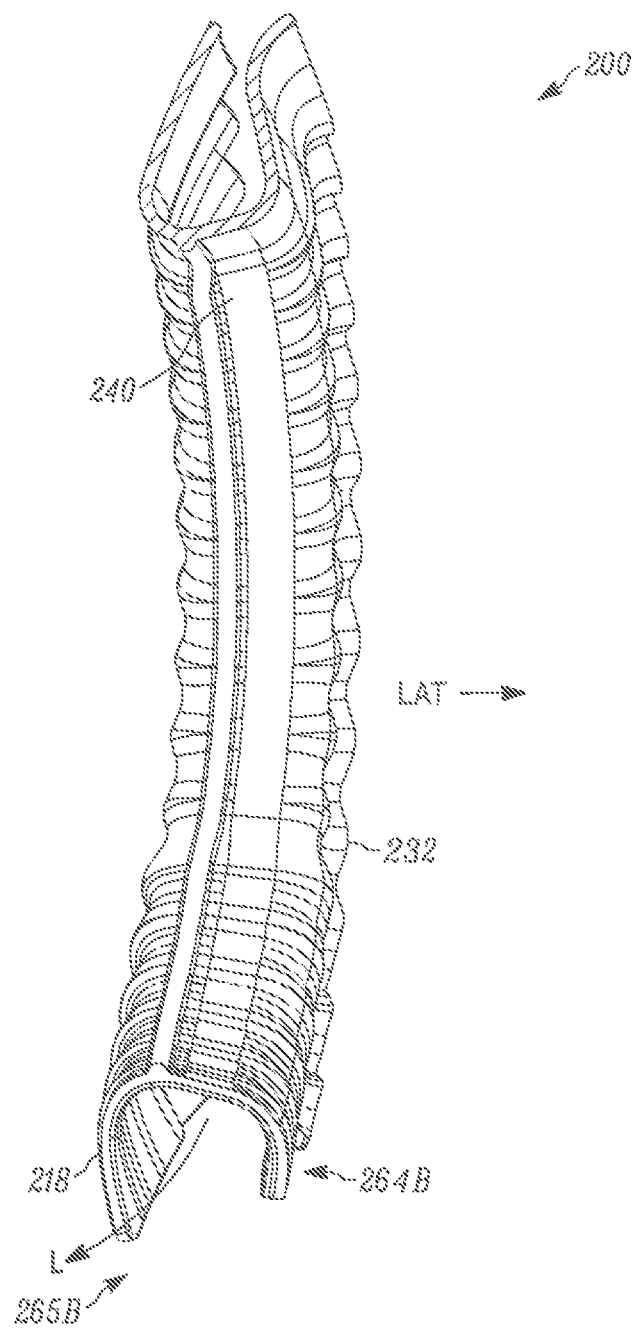
FIG. 20 is an inner section view of FIG. 18 along line 20-20, in accordance with an example embodiment of the present disclosure.

In one example embodiment, the adjustable protective mouth assembly 200 may be inserted into the patient's mouth such that the connection 30 is formed beneath the nose of the patient and the connecting portion 228 is inserted along the bottom lip of the patient. In one example embodiment, such as illustrated in FIGS. 18-20, a first tapered portion 264A is formed on the first end 216 of the first leg 230 and a second tapered portion 264B is formed on a second end 218 of the second leg 232. Responsive to the connection 30 being formed between the first end 216 and the second end 218, the first tapered portion 264A and the second tapered portion 264B form a tapered portion 264, as illustrated in FIG. 19. The tapered portion 264 may be oriented to conform to the inner portion of the upper lip, such as when the upper lip is shortened responsive to the retraction of the retractor.

As best seen in FIGS. 18 and 20, the first end 216 comprises a first outer tapered portion 265A and the second end 218 comprises a second outer tapered portion 265B. Responsive to the connection 30 being formed between the first end 216 and the second end 218, an outer tapered portion (comprising a mirror image of FIG. 19 where reference character 264 would change to 265) may be formed laterally opposite of the tapered portion 264. In an example embodiment, the midline of the upper lip is substantially centrally located about the tapered portion 264 and/or the outer tapered portion 265. The shortening of the upper lip may shorten a distance between the upper lip and the nose. The outer tapered portion may improve a fit of the adjustable protective mouth assembly 200 relative to the nose of the patient, such as when the upper lip is shortened. It is understood that the first end 216 and the second end 218 may comprise the first tapered portion 264A and the second tapered portion 264B, respectively, the first outer tapered portion 265A and the second outer tapered portion 265B, respectively, or both. It should be appreciated that the tapered portion 264 and/or the outer tapered portion 265 could be located at other positions within the mouth without departing from the spirit of the present disclosure. Moreover, in another example embodiment, the assembly 200 could have multiple tapered portions 264, 265 around the perimeter of the assembly.

Figure 21:
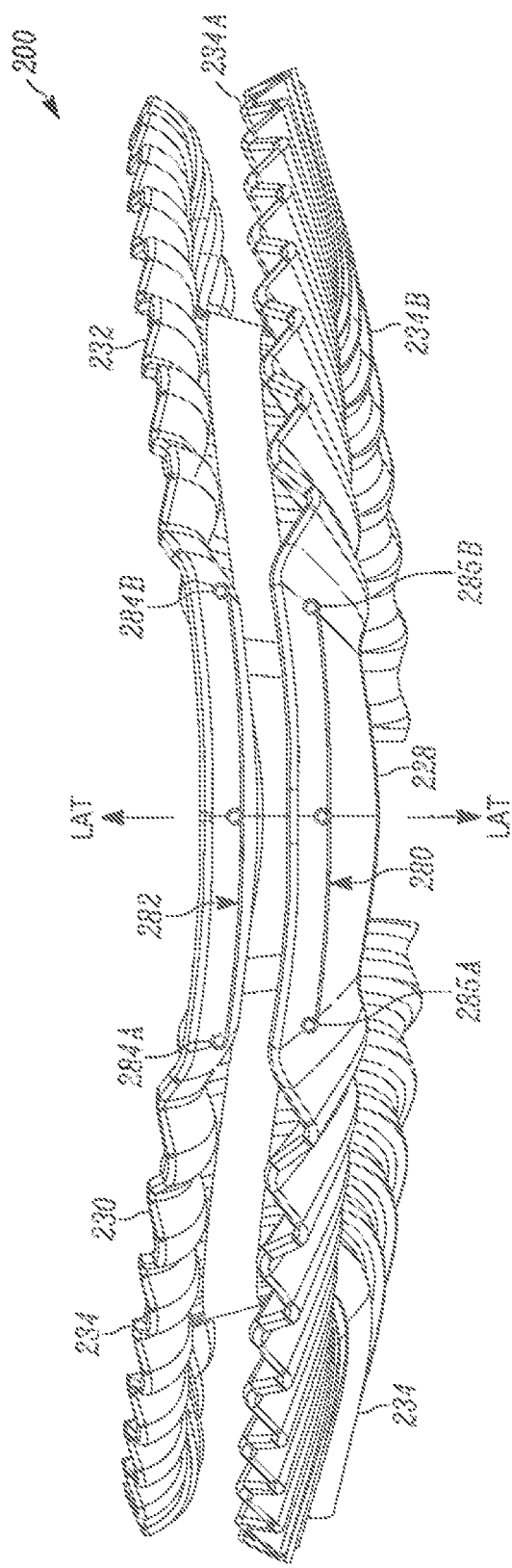
FIG. 21 is a top perspective view of a protective mouth assembly comprising a hinge joint constructed in accordance with an example embodiment of the present disclosure.
Figure 22:
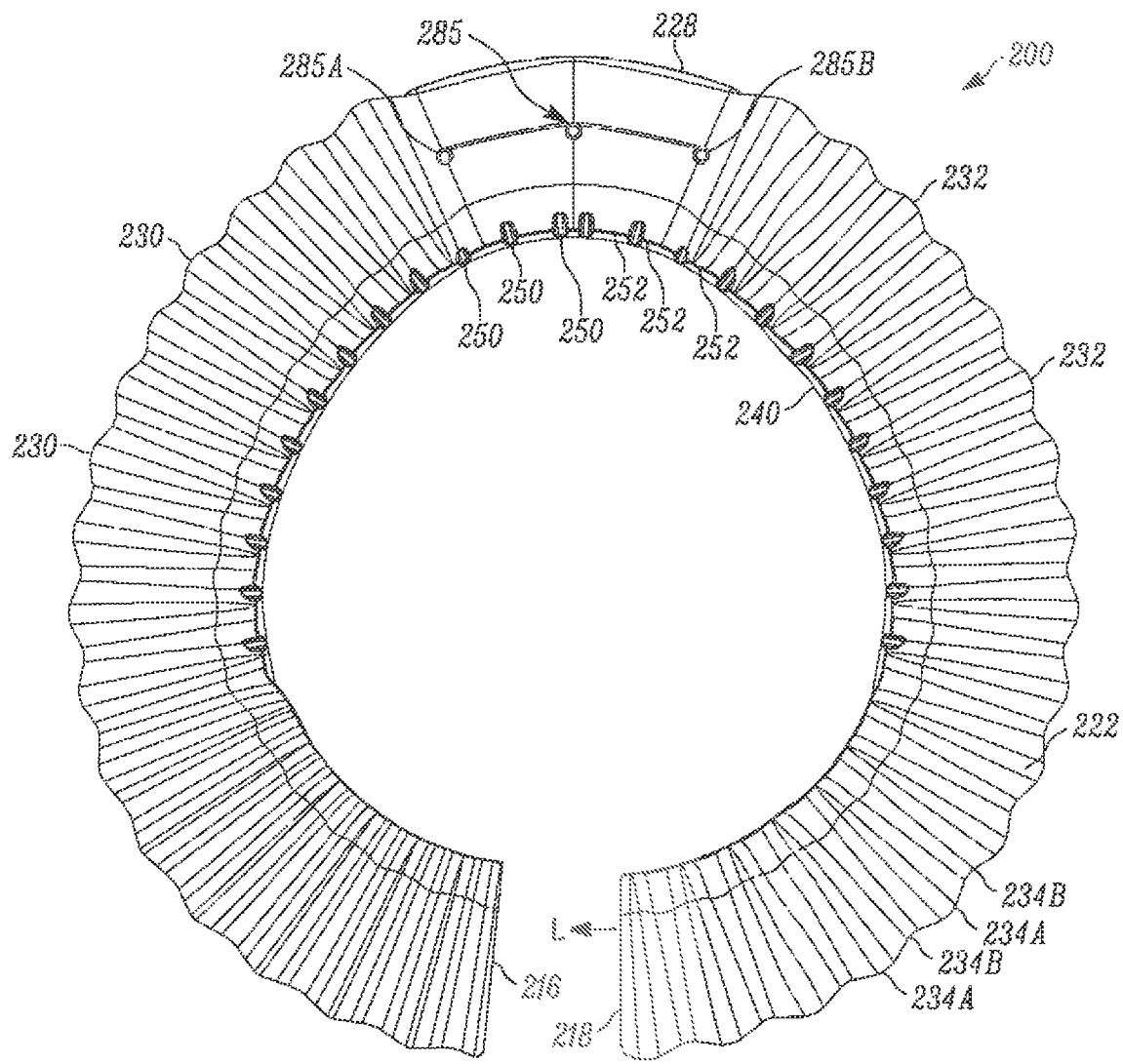
FIG. 22 is a front elevation view of FIG. 21 constructed in accordance with an example embodiment of the present disclosure.

In an embodiment, as illustrated in FIGS. 21-22, the connecting portion 228 comprises at least one of a first hinge joint 280 and a second hinge joint 282. In one example embodiment, the first hinge joint 280 is laterally opposite the second hinge joint 282. The first leg 230 is operably connected to a first arm 285A of the first hinge joint 280 and to a first arm 284A of the second hinge joint 282. The second leg 232 is operably connected to a second arm 285B of the first hinge joint 280 and to a second arm 284B of the second hinge joint 282. At least one of the first hinge joint 280 or the second hinge joint 282 allows adjustment of a position of the first leg 230 relative to the second leg 232 from at least a first hinge angle to a second hinge angle.

In one example embodiment, the hinge joints 280, 282 are co-molded into the assembly 200 and constructed with the same material as the body 222. In an alternative example embodiment, the hinge joints 280 and 282 are springs made from plastic or metal and co-molded with the body 222.

Responsive to the connection 30 being formed between the first end 216 and the second end 218, the adjustment of a position alters a circumference of the adjustable protective mouth assembly 200. In one example embodiment, such as when the first hinge angle is greater than the second hinge angle, the circumference of the adjustable protective mouth assembly 200 is decreased. In another example embodiment, the first hinge joint 280 bends along a first plane (e.g., a plane running from left to right on the page) and the second hinge joint 282 bends along a second plane, the first plane in parallel with the second plane. In another example embodiment, the connecting portion 228 comprises a single hinge joint (not shown), such as located along the radial inner surface 240. The single hinge joint may adjust the first leg 230 and the second leg 232 in a substantially similar manner as the first hinge joint 280 and the second hinge joint 282.

Figure 23:
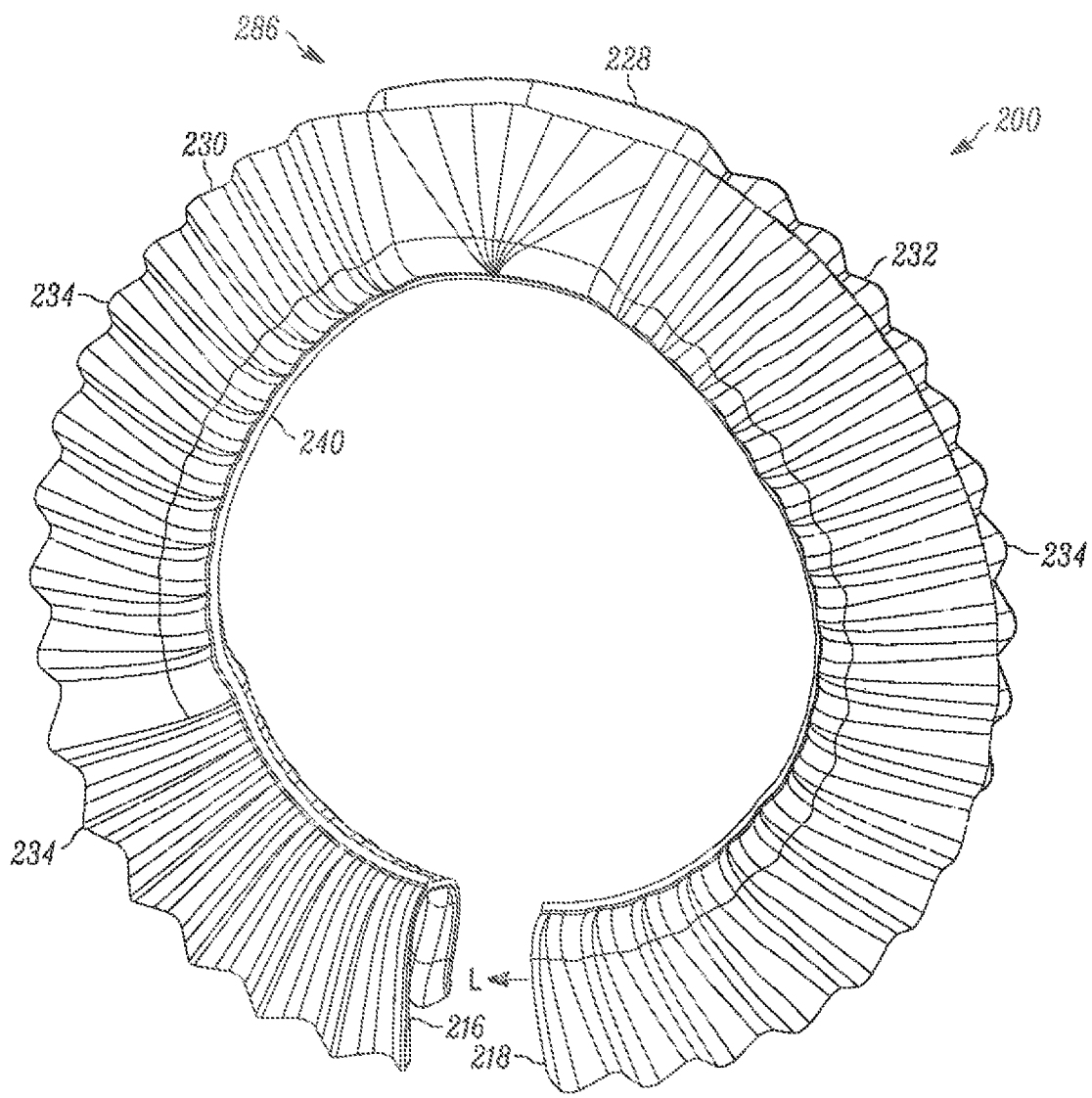
FIG. 23 is a perspective view of a protective mouth assembly comprising a bellowed joint constructed in accordance with an example embodiment of the present disclosure.

In an embodiment, as illustrated in FIG. 23, the connecting portion 228 comprises a bellowed joint 286. In one example embodiment, the bellowed joint 286 comprises a plurality of rib structures in a fan configuration, such that the ribs are more compact at a base of the bellowed joint 286, nearer the inner radial surface 240, and less compact at the top of the bellowed joint 286, opposite the inner radial surface 240. In one example embodiment, the bellowed joint 286 is operably connected to the first leg 230 and the second leg 232. The bellowed joint 286 may allow adjustment of the position of the first leg 230 relative to the second leg 232 from a first bellowed angle to a second bellowed angle. Wherein, responsive to the connection 30 being formed between the first end 216 and the second end 218, the adjustment of the position alters the circumference of the adjustable protective mouth assembly 200. In one example embodiment, the bellowed joint 286 is designed to bend across multiple planes (e.g., from left to right on the page, and into and out of the page). It should be appreciated that such structures having ribs 234 and bellows 286 throughout the entire assembly 200, as shown in FIG. 23, allows for maximizing bending and/or flexibility.

Figure 24:
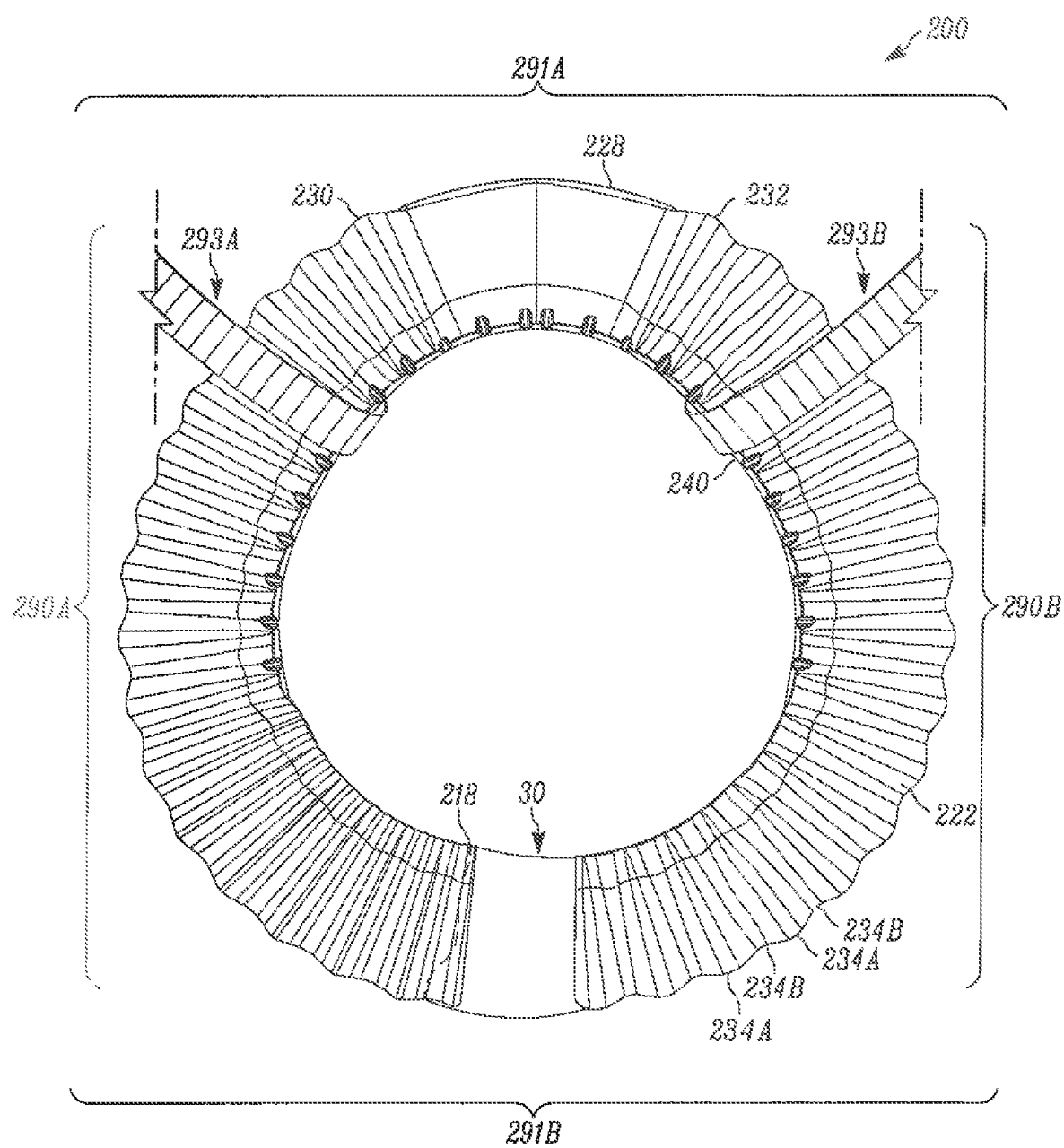
FIG. 24 is a front elevation view of a protective mouth assembly interacting with a retractor constructed in accordance with an example embodiment of the present disclosure.

In another example embodiment, as illustrated in FIG. 24, a material thickness of an upper portion 291A and a lower portion 291B of the adjustable protective mouth assembly 200 are relatively less thick (e.g., two or three times less thick) than a material thickness of a first side 290A and a second side 290B of the adjustable protective mouth assembly 200, thus providing flexibility to the connecting portion 228 and the connection 30 comprised by the first end 216 and the second end 218, while increasing the protection and stability provided by the first side 290A and the second side 290B. The adjustable protective mouth assembly 200 may be inserted into the mouth in a first configuration, such that the upper portion 291A is beneath the nose, or in a second configuration, such that the connection comprised by the first end 216 and the second end 218 is beneath the nose. In one example embodiment, in either configuration, a retractor 293 may be used in conjunction with the adjustable protective mouth assembly 200. A first arm 293A of the retractor 293 may be installed over the first side 290A and a second arm 293B of the retractor 293 may be installed over the second side 290B. It is understood that though the retractor 293 is depicted nearer the connecting portion 228 than the connection 30, the retractor 293 may be utilized relative to any portion or side of the protective mouth assembly 200. The increased thickness along the first side 290A and the second side 290B may increase stability of the adjustable protective mouth assembly 200 when used in conjunction with the retractor 293.

In the foregoing specification, specific embodiments have been described. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. In one non-limiting embodiment the terms are defined to be within for example 10%, in another possible embodiment within 5%, in another possible embodiment within 1%, and in another possible embodiment within 0.5%. The term "coupled" as used herein is defined as connected or in contact either temporarily or permanently, although not necessarily directly and not necessarily mechanically. A device or structure that is "configured" in a certain way is configured in at least that way, but may also be configured in ways that are not listed.

To the extent that the materials for any of the foregoing embodiments or components thereof are not specified, it is to be appreciated that suitable materials would be known by one of ordinary skill in the art for the intended purposes.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An adjustable protective mouth assembly for protecting the oral cavity and surround of a patient, the adjustable protective mouth assembly comprising:
   a first leg and a second leg having channeled bodies for inserting into the oral cavity of a patient during use, said channeled bodies formed for receiving a lip of a patients therewithin; and
   a connecting portion spacing said first leg from said second leg, said connecting portion integrally formed with said first and second legs, said first and second legs extending transversely and flexibly from said connecting portion, further wherein, the first and second leg are movable toward and away from each other to adjust to fit within an oral cavity.

2. The adjustable protective mouth assembly of claim 1 wherein said first leg is substantially the same length as said second leg.

3. The adjustable protective mouth assembly of claim 2 wherein said first leg comprises a plurality of ribs.

4. The adjustable protective mouth assembly of claim 2 wherein said first leg and said second leg comprises a plurality of ribs.

5. The adjustable protective mouth assembly of claim 1 wherein said first leg is coupled to the connecting portion by a first flexible joint, said first flexible joint allowing for lateral movement of said first leg relative to said second leg.

6. The adjustable protective mouth assembly of claim 5 wherein said first leg comprises a plurality of ribs.

7. The adjustable protective mouth assembly of claim 5 wherein said first leg and said second leg comprises a plurality of ribs.

8. The adjustable protective mouth assembly of claim 1 wherein said second leg is coupled to the connecting portion by a second flexible joint, said second flexible joint allowing for lateral movement of said second leg relative to said connecting portion.

9. The adjustable protective mouth assembly of claim 8 wherein said first leg comprises a plurality of ribs.

10. The adjustable protective mouth assembly of claim 8 wherein said first leg and said second leg comprises a plurality of ribs.

11. The adjustable protective mouth assembly of claim 1 wherein a first leg wall of the first leg comprises a plurality of ribs.

12. The adjustable protective mouth assembly of claim 1 wherein a first leg wall of the first leg and a second leg wall of the second leg comprises a plurality of ribs.

13. An adjustable protective mouth assembly for protecting the surroundings adjacent to the oral cavity of a patient, the adjustable protective mouth assembly comprising:
   a channeled body having a first leg and a second leg spaced and integrally coupled by a connecting portion, said channeled body for inserting into the oral cavity of a patient during use;
   said channeled body further comprising a first end and a second end, such that the channeled body of said first end is constructed to be received and nest within the channeled body of said second end, forming a connection therebetween said first end and said second end to further form a continuous adjustable protective mouth assembly; and
   wherein said connecting portion comprises a line of weakness between said first leg and said second leg such that when said connection is formed, said line of weakness allows adjustment of a position of the first leg relative to the second leg from a first line of weakness angle to a second line of weakness angle to alter the circumference of said assembly.

14. The adjustable protective mouth assembly of claim 13 wherein said line of weakness provides the maximum flexibility and bending between said first end and said second end while keeping said first end connected to said second end.

15. The adjustable protective mouth assembly of claim 14 wherein said line of weakness provides for the bending across multiple planes.

16. The adjustable protective mouth assembly of claim 15 wherein said line of weakness is a bellowed joint.

17. The adjustable protective mouth assembly of claim 14 wherein said line of weakness is a bellowed joint.

18. The adjustable protective mouth assembly of claim 13 wherein said line of weakness is a bellowed joint.

19. The adjustable protective mouth assembly of claim 13 wherein said line of weakness provides for the bending across multiple planes.

20. The adjustable protective mouth assembly of claim 13 wherein said line of weakness is a bellowed joint.

21. The adjustable protective mouth assembly of claim 13 wherein said line of weakness is a hinged joint.

* * * * *